United States Patent [19]

Mauric et al.

[11] 4,388,431
[45] Jun. 14, 1983

[54] FLAMEPROOFED ORGANIC MATERIALS

[75] Inventors: Claudine Mauric, Basel; Rainer Wolf, Allschwil, both of Switzerland

[73] Assignee: Sandoz Ltd., Basel, Switzerland

[21] Appl. No.: 121,205

[22] Filed: Feb. 13, 1980

[30] Foreign Application Priority Data

Feb. 14, 1979 [CH] Switzerland ........................ 1461/79
Feb. 23, 1979 [CH] Switzerland ........................ 1839/79

[51] Int. Cl.$^3$ .......................... C08K 5/52; C08K 5/53
[52] U.S. Cl. ...................................... 524/119; 57/904; 521/907; 524/710
[58] Field of Search ...................... 260/45.7 P, 45.8 R, 260/927 R, 985, 45.85 R, 932, 937; 524/119, 710

[56] References Cited

U.S. PATENT DOCUMENTS

| | | | |
|---|---|---|---|
| 2,495,108 | 1/1950 | Kosolapoff | 260/927 R |
| 2,634,288 | 4/1953 | Boyer et al. | 260/932 |
| 2,952,701 | 9/1960 | McConnell et al. | 260/927 R |
| 2,974,158 | 3/1961 | Lanham | 260/927 R |
| 3,027,395 | 3/1962 | Sharp et al. | 260/985 |
| 3,155,639 | 11/1964 | Emmons et al. | 260/985 |
| 3,801,677 | 4/1974 | Baranauckas et al. | 260/937 |
| 3,890,409 | 6/1975 | Mayerhoefer et al. | 260/927 R |
| 3,922,323 | 11/1975 | Reese et al. | 260/927 R |
| 3,970,635 | 7/1976 | Lawton et al. | 260/927 R |
| 4,067,931 | 1/1978 | Batorewicz | 260/927 R |
| 4,077,940 | 3/1978 | Wedel | 260/45.7 P |
| 4,143,101 | 3/1979 | Mayerhoefer et al. | 260/927 R |
| 4,148,782 | 4/1979 | Mauric et al. | 524/119 |
| 4,181,646 | 1/1980 | Moedritzer | 260/927 R |
| 4,242,138 | 12/1980 | Mauric et al. | 106/18.18 |
| 4,268,459 | 5/1981 | Hoffman | 260/927 R |

FOREIGN PATENT DOCUMENTS

1543394 3/1971 Fed. Rep. of Germany .
2728595 1/1978 Fed. Rep. of Germany .

OTHER PUBLICATIONS

Denney et al., Jour. ACS, vol. 88, No. 8, 1966, pp. 1830 and 1831.
Maier, Syn. React. Inorg. Metal-Org. Chem., 6(2), 1976, pp. 133-155.
Science, vol. 182, 1973, pp. 1135 and 1136.

Primary Examiner—John Kight, III
Assistant Examiner—R. A. White
Attorney, Agent, or Firm—Gerald D. Sharkin; Richard E. Vila; Thomas C. Doyle

[57] ABSTRACT

A group of diphosphonic acid tetra-esters and phosphonic or thiophosphonic acid O,O,O-triesters containing dioxaphosphorinane rings are useful as flame retardants for polymeric organic materials, particularly polyesters. The compounds, some of which are novel, are prepared by reaction of the corresponding phosphites with peroxy compounds or with sulphur.

23 Claims, No Drawings

FLAMEPROOFED ORGANIC MATERIALS

This invention relates to flameproofed polymeric organic materials containing, as flameproofing agents, organic phosphorus compounds.

The invention provides flameproofed polymeric organic materials containing a compound of formula I

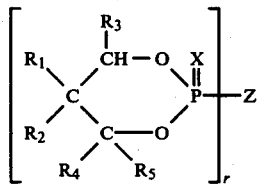
I in which
R$_1$ and R$_2$ are independently hydrogen, C$_{1-4}$alkyl or phenyl; or R$_1$ and R$_2$ together with the carbon atom to which they are attached form a cyclohexylidene or cyclohexenylidene ring,
R$_3$ and R$_4$ are independently hydrogen or C$_{1-4}$alkyl,
R$_5$ is hydrogen or methyl
provided that when R$_1$ and R$_2$ together with the carbon atom to which they are attached form a ring, then R$_3$, R$_4$ and R$_5$ are all hydrogen,
Z is a group Z$_a$ or Z$_b$ as defined below,
X is oxygen when Z is Z$_a$ and oxygen or sulphur when Z is Z$_b$,
r is 2 when Z is Z$_a$ and 2, 3 or 4 when Z is Z$_b$, Z$_a$ is methylene, ethylene, phenylethylene, C$_{3-12}$ alkylene unsubstituted or substituted by up to 2 groups selected from phenyl and phenoxy, C$_{4-8}$ cycloalkylene unsubstituted or substituted by up to 2 groups selected from phenyl and phenoxy, C$_{4-12}$alkenylene in which the double bond is not in a terminal position, C$_{4-12}$alkynylene in which the triple bond is not in a terminal position, or a group —C$_n$H$_{2n}$—A—C$_n$H$_{2n}$—,

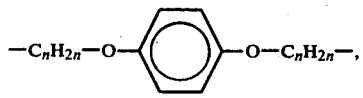

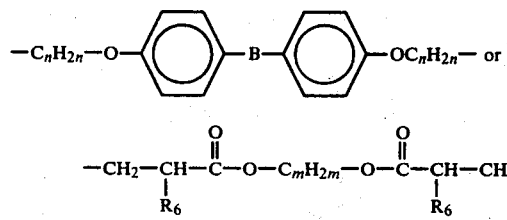

in which
A is C$_{4-8}$cycloalkylene or phenylene
B is

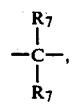

—CH$_2$CH$_2$—, —O— or —SO$_2$—

R$_6$ is hydrogen or methyl
R$_7$ is hydrogen or C$_{1-4}$alkyl
n is an integer from 2 to 5 and
m is an integer from 2 to 12
and Z$_b$, when r=2 is

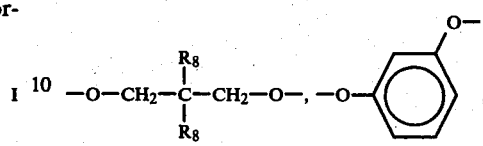

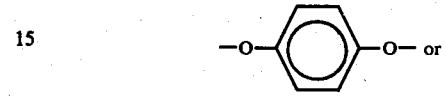

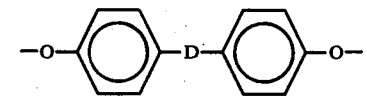

where R$_8$ is C$_{1-4}$alkyl, phenyl, —CH$_2$Cl or —CH$_2$Br and D is

—O— or —SO$_2$— provided that when X is oxygen, —Z$_b$— may not be —O—C$_6$H$_4$—O— or

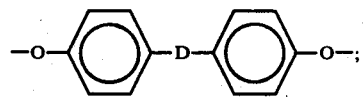

when r=3, is

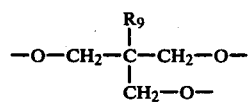

where R$_9$ is methyl or ethyl
and when r=4, is

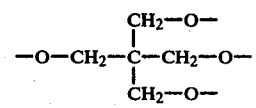

provided that when Z is Z$_b$, the polymeric organic material is other than cellulose or a cellulose derivative.

Where any symbol, for example n, R$_6$, R$_7$ or R$_8$, appears more than once in a formula, it is to be understood that it may have the same or different significances, unless otherwise stated. All groups capable of bearing substituents are unsubstituted unless otherwise stated. All alkylene groups, including C$_2$H$_{2n}$ and C$_m$H$_{2m}$, may, unless otherwise stated, be linear or branched, but are preferably linear.

Preferred significances of R$_1$ and R$_2$ are R$_1'$ and R$_2'$, where R$_a'$ and R$_2'$ are, independently, C$_{1-4}$alkyl or phenyl; more preferably they are $R_1''$ and $R_2''$ where $R_1''$ and $R_2''$ are, independently, $C_{1-4}$alkyl, even more preferably they are $R_1'''$ and $R_2'''$ where $R_1'''$ and $R_2'''$ are, independently, $C_{1-3}$alkyl, particularly methyl. When $R_1$ and $R_2$ are both alkyl, they are preferably the same.

$R_3$ is preferably $R_3'$ where $R_3'$ is hydrogen or $C_{1-3}$alkyl, more preferably $R_3''$ where $R_3''$ is hydrogen, n-propyl or isopropyl, particularly hydrogen.

$R_4$ is preferably hydrogen.

$R_5$ is preferably hydrogen.

$Z_a$ is preferably $Z_a'$ where $Z_a'$ is $C_{1-10}$alkylene, $C_{4-8}$cycloalkylene, 2-butenylene, 2-butynylene, $-C_nH_{2n}-A-C_nH_{2n}-$

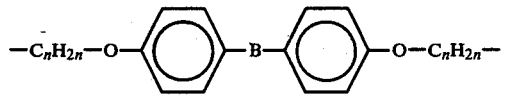

or $-CH_2CHR_6-COO-C_mH_{2m}-OOC.CHR_6CH_2-$ where A, B, $R_6$, n and m are as defined above.

More preferably $Z_a$ is $Z_a''$, that is, $C_{1-10}$alkylene, $C_{4-8}$cycloalkylene, 2-butenylene, 2-butynylene,

or $-CH_2CHR_6-COO-C_{m'}H_{2m'}-OOC-CHR_6CH_2-$ where
n' is 2 or 3 and
m' is 2 to 6.

Particularly preferred significances of $Z_a$ are given by $Z_a'''$ where $Z_a'''$ is $C_{1-10}$alkylene, $C_{6-8}$cycloalkylene, 2-butenylene or $-CH_2CHR_6-COO-C_{m''}H_{2m''}-OOC-CHR_6CH_2-$ where m'' is 2, 3 or 4.

$Z_a$ as $C_{1-10}$alkylene is preferably ethylene, propylene, butylene, hexylene or decylene, particularly ethylene, butylene, hexylene or decylene.

In $Z_a$,
A is preferably p-phenylene or 1,4-cyclohexylene, particularly p-phenylene;
B is preferably

or oxygen, particularly

$R_7$ is preferably methyl or ethyl, particularly methyl;
n is preferably n', defined above, and both n's in the formula are preferably the same; and
m is preferably m', more preferably m'', defined above; r, when Z is $Z_b$ is preferably 2 or 3, more preferably 2.

When r is 2, $Z_b$ is preferably $Z_b'$ where $z_b'$ is

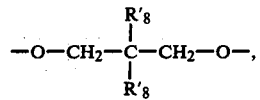

where $R_8'$ is $C_{1-4}$alkyl or phenyl, more preferably $Z_b''$ where $Z_b''$ is

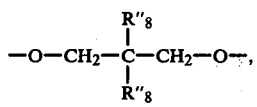

where $R_8''$ is $C_{1-4}$alkyl.

In $Z_b$, $R_8$ is preferably $R_8'$, defined above, more preferably $R_8''$, defined above, still more preferably $R_8'''$, that is, $C_{1-3}$alkyl, particularly methyl. Preferably both $R_8$'s are the same.

Of the compounds of formula I in which Z is $Z_a$, the compounds of formula $I_a'$

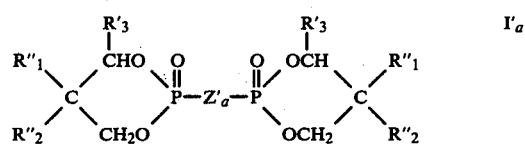

are preferred, particularly those of formula $I_a''$

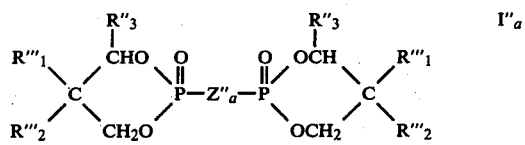

and especially those of formula $I_a'''$

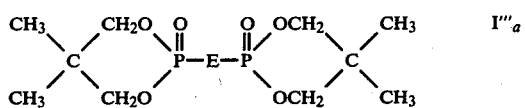

in which E is $C_{1-10}$alkylene.

Of the compounds of formula I in which Z is $Z_b$, the compounds of formula $I_b'$

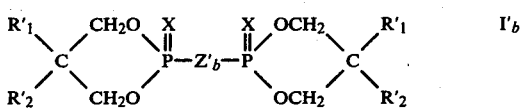

are preferred, particularly those of formula $I_b''$

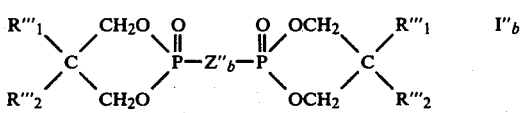

and especially the compound of formula $I_b'''$

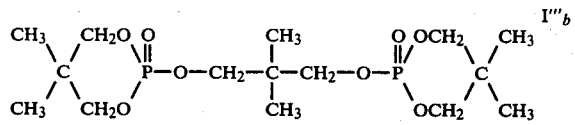

Compounds of formula II

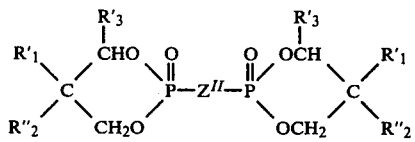

in which
$R_1'$ is $C_{1-4}$alkyl or phenyl,
$R_2''$ is $C_{1-4}$alkyl,
$R_3'$ is hydrogen or $C_{1-3}$alkyl,
$Z^{II}$ is $Z_a^{II}$ or $Z_b^{II}$ where
$Z_a^{II}$ is ethylene, propylene, $C_{5-10}$alkylene, $C_{6-8}$cycloalkylene, 2-butenylene, 2-butynylene

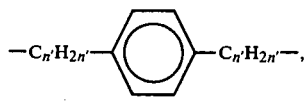

or $-CH_2CHR_6-COO-C_{m'}H_{2m'}-OOC-CHR_6CH_2-$ where
$n'$ is 2 or 3, $m'$ is 2 to 6 and
$R_6$ is hydrogen or methyl, and
$Z_b^{II}$ is

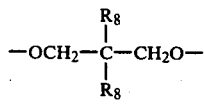

where $R_8$ is as defined above provided that, when both $R_1''$'s and both $R_2'''$'s are methyl and $R_3'$ is hydrogen, then at least one of the groups $R_8$ is other than methyl,
are new, and constitute a further aspect of the present invention. Of these novel compounds, those in which $Z^{II}$ is $Z_a^{II}$ are preferred, preferably those in which $Z_a^{II}$ is alkylene, more preferably those in which $Z_a^{II}$ is linear $C_{5-10}$alkylene.

The invention also provides a process for the preparation of compounds of formula I in which X is oxygen characterised in that a compound of formula III

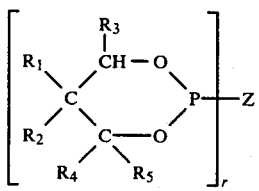

in which $R_1-R_5$, r and Z are as defined above, is oxidized with a peroxy compound, preferably a per-acid. More particularly, the invention provides a process for the preparation of compounds of formula II characterised in that a compound of formula IV

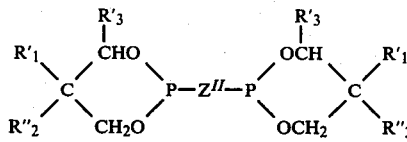

in which $R_1'$, $R_2''$, $R_3'$ and $Z^{II}$ are as defined above, is oxidized with a peroxy compound, preferably a peracid.

Compounds of formula I in which X is sulphur may be prepared by addition of sulphur to compounds of formula III in conventional manner.

Compounds of formula II in which $Z^{II}$ is $Z_a^{II}$ may also be prepared by the reaction of 2 moles of a compound of formula V

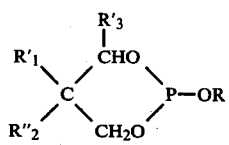

in which R is ethyl or propyl, or of a mixture of such compounds, with 1 mole of a compound of formula VI

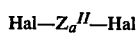

in which
$-Z_a^{II}-$ is as defined above and
Hal is chlorine or bromine, preferably bromine,
the reaction being carried out in conventional manner.

The polymeric organic material containing the compound of formula I may in principle be any inflammable natural or synthetic organic polymer to which it is desired to impart flame-resistance, provided however that when Z in formula I is $Z_b$, i.e. when the compound of formula I is an 0,0,0-triester of phosphoric or thiophosphoric acid, the organic polymer is not cellulose or a cellulose derivative.

Suitable organic polymers include polyolefins, for example polyethylene, polypropylene, ethylene-propylene copolymers, polystyrene and ABS resins; polyacrylonitrile; polymethyl methacrylate; polyesters for example polybutyleneterephthalate and particularly, polyethyleneterephthalate; unsaturated polyester resins; polyamides, for example nylon-6 and nylon-66; polyphenylene oxide; polycarbonate; polyurethanes and synthetic resins such as paints and varnishes. For the diphosphonic acid tetraesters, i.e. the compounds of formula I in which Z is $Z_a$, natural or regenerated cellulose and cellulose esters for example cellulose 2½-acetate or cellulose triacetate may also be used.

Preferably the flameproofed organic polymeric material of the invention is a thermoplastic, particularly a polyolefin, polyester, polyamide, polycarbonate or polyurethane containing a compound of formula I. More preferably it is a polyurethane or polyester, particularly polyethylene terephthalate.

The polymeric organic material may for example be in the form of bulk powder, granules or pellets suitable for further processing; in the form of fires, film, foam or shaped articles formed e.g. by vacuum, compression or injection moulding; or in the form of woven or knitted textile fabrics or finished articles for example articles of clothing.

The polymeric organic material contains an effective flame-retarding amount of the compound of formula I, or, of course, of a mixture of one or more compounds of formula I, but this amount will vary within wide limits, depending upon the chemical nature and physical form of the material. In general, the material will contain from 0.1 to 40%, preferably from 0.5 to 20% by weight of the compound of formula I. For polyester, the content of compound of formula I is preferably 0.5 to 10, more preferably 1 to 5% by weight; for polyurethanes preferably 2.5 to 15%, more preferably 5 to 10% by weight; for polymethyl methacrylate preferably 5 to 20%, more preferably 8 to 15% by weight; for cellulose acetate preferably 0.5 to 10, more preferably 1 to 5% by weight.

The polymeric organic materials may contain other additives in addition to the compounds of formula I. These may be other types of flame-retardants, with which the compounds of formula I may have an additive or synergistic effect, or may be other types of additives conventionally used in such materials, for example heat and/or UV-stabilizers, antioxidants, dyes, pigments, optical brighteners, plasticizers, anti-static agents, etc. Such other additives may be surface-coated on the organic material, incorporated into the bulk of the material, or even co-polymerised with the corresponding monomer.

The invention also provides a process for the flameproofing of a polymeric organic material characterised by the incorporation of one or more compounds of formula I into the organic material before, during or after polymerisation, whereby when the compound of formula I is a phosphoric or thiophosphoric acid 0,0,0-triester, the polymeric organic material is other than cellulose or a cellulose derivative.

The incorporation may be carried out by standard methods, depending upon the nature of the polymeric material. For example for certain types of polymers the compound of formula I may be mixed with the monomer or prepolymer and the mixture subjected for example to addition polymerisation (e.g. for polymethyl methacrylate) or to polycondensation (e.g. for polyesters). The compound of formula I may also be blended with molten polymer for example polyester, before or during processing into shaped articles such as injection moulded articles, extruded film or fibres. The compound of formula I may also be added to a solution from which a fibre or film may be formed by evaporation of solvent or by precipitation in a suitable bath, for example for polyacrylonitrile, polymethyl methacrylate and, with the diphosphonic acid tetra-esters, for regenerated cellulose and cellulose acetate. Preferably, the compound of formula I, particularly the compound of formula $I_b'''$, is incorporated into polyethylene terephthalate by melt blending.

For the incorporation of compound of formula I in polymeric organic materials, by melt blending or otherwise, it may be advantageous to add the compound of formula I in the form of a concentrate or master-batch composition containing for example 20 to 90%, preferably 30 to 60% by weight, of compound of formula I. The remainder of the composition may comprise the same polymeric organic material as that which is to be flameproofed, optionally together with one or more other additives for example stabilizers, antioxidants, etc. Such concentrate or master-batch compositions also form part of the present invention.

Compounds of formula I give good flame-retardant effects at relatively low concentrations, particularly in polyesters, and are relatively chemically inert to polyesters under melt-processing conditions.

The following Examples in which all parts and percentages are by weight and temperatures are in degrees Centigrade, illustrate the invention.

PREPARATION OF COMPOUNDS OF FORMULA I

Each preparation of a compound which is believed to be novel constitutes an example of the invention and is assigned an example number. Preparations of compounds believed to be known are assigned a compound number C1, C2 etc.

EXAMPLE 1

35.6 Parts 5,5-dimethyl-2-ethoxy-1,3-2-dioxaphosphorinane, 18.8 parts 1,2-dibromoethane and 0.48 parts $NiCl_2.6H_2O$ are warmed to 130°–135° C. over 2 hours and finally stirred for 6 hours at this temperature. The mixture is cooled to room temperature, and the resulting thick suspension is diluted with 43 parts diethyl ether, filtered and washed with 20 parts diethyl ether, to give 8.5 parts of the compound of formula

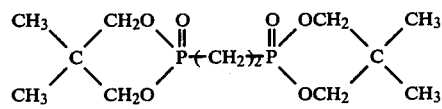

m.p. 219°–221° C.

EXAMPLES 2–5,

Compounds C1, C2

In analogous manner, using appropriate dibromo compounds, compounds of formula

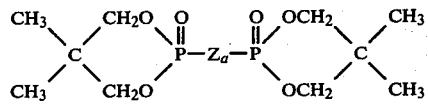

in which $Z_a$ is as shown in Table 1, are obtained.

TABLE 1

| Example or Compound No. | $Z_a$ | m.p. °C. |
|---|---|---|
| C1 | —$CH_2$— | 196–197 |
| 2 | $(CH_2)_3$ | 171–175 |
| C2 | $(CH_2)_4$ | 222–225 |
| 3 | $(CH_2)_5$ | 134–136 |
| 4 | $(CH_2)_6$ | 179–181 |
| 5 | $(CH_2)_{10}$ | 169–171 |

Compound C3

88.5 Parts of the compound of formula

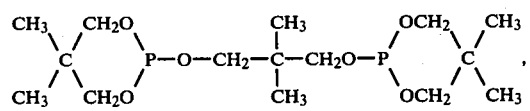

prepared by the method described in J. Org. Chem. 24 (1959), 630, is dissolved in 650 parts 1,2-dichloroethane. To this solution is added dropwise over 70 minutes 90.2 parts 3-chloroperbenzoic acid dissolved in 1125 parts 1,2-dichloroethane, cooling gently with ice to maintain the temperature at 20°–30° C. Finally, the reaction mixture is stirred 16 hours under reflux then cooled to 0°–5° for 30 minutes, when 3-chlorobenzoic acid precipitates. The mixture is filtered and the filtrate is tested to ensure that no peroxides are present, then shaken with 1000 parts 2% caustic soda solution, washed with water until neutral then dried over magnesium sulphate. After drying the solvent is distilled off, leaving 61 parts of a slightly resinous yellow product, which is then made into a paste with 70 parts diethyl ether, filtered after 1 hour and dried. The crude product (45 parts, m.p. 126°–128°) is recrystallised from 1680 parts carbon tetrachloride, giving 40 parts of the compound of formula $$\begin{array}{c}CH_3\\ \diagdown\\ CH_3\end{array}\!\!\!C\!\!\!\begin{array}{c}CH_2O\\ \diagup\\ CH_2O\end{array}\!\!\!\begin{array}{c}O\\ \|\\ P\end{array}\!\!-OCH_2-\!\!\begin{array}{c}CH_3\\ |\\ C\\ |\\ CH_3\end{array}\!\!-CH_2O-\!\!\begin{array}{c}O\\ \|\\ P\end{array}\!\!\!\begin{array}{c}OCH_2\\ \diagup\\ OCH_2\end{array}\!\!\!C\!\!\!\begin{array}{c}CH_3\\ \diagdown\\ CH_3\end{array}$$

m.p. 128°–130°.

Compound C4

In analogous manner, the corresponding pentaerythritolester of formula $$\left[\begin{array}{c}CH_3\\ \diagdown\\ CH_3\end{array}\!\!\!C\!\!\!\begin{array}{c}CH_2O\\ \diagup\\ CH_2O\end{array}\!\!\!\begin{array}{c}O\\ \|\\ P\end{array}\!\!-OCH_2\!\!-\!\right]_4\!\!C$$

may be prepared, m.p. 270°.

Compounds C5–C7

Compounds of formula $$\left[\begin{array}{c}CH_3\\ \diagdown\\ CH_3\end{array}\!\!\!C\!\!\!\begin{array}{c}CH_2O\\ \diagup\\ CH_2O\end{array}\!\!\!\begin{array}{c}S\\ \|\\ P\end{array}\!\!-\!\right]_r\!\!Z_b$$

in which $r$ and $Z_b$ are as given in Table 2, are prepared by reaction of the corresponding trivalent compounds with sulphur, suitably in an inert organic solvent.

TABLE 2

| Compound No. | r | $Z_b$ | m.p. °C. |
|---|---|---|---|
| C5 | 2 | $-OCH_2-\underset{\underset{CH_3}{\mid}}{\overset{\overset{CH_3}{\mid}}{C}}-CH_2O-$ | 164–165 |
| C6 | 4 | $C(CH_2O)_4$ | 240–242 |
| C7 | 2 | $-O-\!\!\bigcirc\!\!-O-$ | 204–206 |

PREPARATION OF FLAMEPROOFED POLYMERS

EXAMPLE 6

400 Parts polyethylene terephthalate granules were mixed in a tumbler mixer with 12 parts of compound C3 at room temperature for 30 minutes. The mixture was then extruded in a laboratory extruder at 250° to 260°, and the granulate so obtained was dried for 16 hours at 140° and finally spun into fibres on a laboratory spinning apparatus at 285°. The fibres, which were drawn at a 1:4 draw ratio and had an individual thickness of 9.6 den, were woven into a fabric of weight 130 g/m², into which several rows of glass fibre were stitched. The finished fabric was subjected to the limiting oxygen index (LOI) test for flammability, as described by Fenimore and Martin (see Modern Plastics, November 1966), which indicated a very good flameproofing effect for Compound C3.

EXAMPLE 7

100 Parts polypropylene powder (Propathene GW 522M) were mixed well with 6 parts of Compound C2 and the mixture was melt blended on a roll mill at 165°–175° for 5 minutes. The resulting molten blend was press-moulded into 1 mm thick plates 230° for 3 minutes. The plates were tested for flammability by the LOI test.

EXAMPLE 8

100 Parts of a commercial ABS powder were mixed with 6 parts of the compound of Example 4 on a laboratory roll mill at 160°–170° for 5 minutes, and finally pressed at 220° to 1 mm thick plates. The plates were tested for flammability by the LOI test.

EXAMPLE 9

100 Parts of a commercial polycarbonate powder were dried at 120° for 4 hours, then dry mixed in a shaker with 6 parts of the compound of Example 4. The mixture was extruded at 300° into a strand and chopped into granules. The granulate was further dried 4 hours at 120° and formed into 2 mm thick plates in an injection moulding machine. The plates were tested for flammability by the LOI test.

EXAMPLE 10

100 Parts of polyol (Voranol 4711, Dow Chemical Co.), 1.6 parts of a foam stabiliser, 0.12 parts amine catalyst (Desmorapid DB, Bayer AG), 0.18 parts stannous octoate and 4.8 parts water were stirred for 1 minute in a beaker at 1000–2000 rpm with 17.6 parts of Compound C3. To the mixture was added 58 parts of diisocyanate (Desmodur T80, Bayer AG), with stirring for 10 seconds. The foaming reaction mixture was poured into a mould, left for 2 hours at room temperature and finally cured for 2 hours at 60°. An even polyurethane foam of density 31 kg/m³ was obtained. Test samples were cut from the foam and tested for flammability by the LOI test.

EXAMPLE 11

20 Parts cellulose acetate powder were dissolved by stirring in 80 parts acetone. To the solution was slowly added 0.40 parts of the finely ground compound of Example 3, and the mixture was stirred until the additive was evenly dispersed. The mixture was then poured onto a glass plate and spread out into a fine film. After evaporation of the acetone, the film was removed from the glass plate and dried in an oven at 85° for 30 minutes. The film was tested for flammability by the LOI test.

Examples 6–10 may be repeated using any of the compounds of Examples 1–5 and compounds C1–C7 and Example 11 may be repeated using any of the compounds of Examples 1, 2, 4 and 5 and compounds C1 and C2.

What is claimed is:

1. Flameproofed polyester containing, as a flameproofing agent, a flameproofing effective amount of at least one compound of formula I,

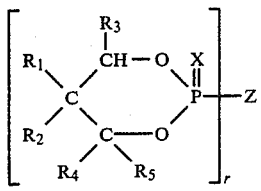

wherein
$R_1$ and $R_2$ are, independently, hydrogen; $C_{1-4}$alkyl; phenyl; or $R_1$ and $R_2$, together with the carbon atom to which they are attached, form a cyclohexylidene or cyclohexenylidene ring;
$R_3$ and $R_4$ are, independently, hydrogen or $C_{1-4}$alkyl;
$R_5$ is hydrogen or methyl, provided that when $R_1$ and $R_2$, together with the carbon atom to which they are attached, form a cyclohexylidene or cyclohexenylidene ring, each of $R_3$, $R_4$ and $R_5$ is hydrogen;
Z is a group $Z_a'''$ or $Z_b$, where
  $Z_a'''$ is $C_{1-10}$-alkylene, $C_{6-8}$cycloalkylene, 2-butenylene or a group of the formula $$-CH_2CHR_6-COO-C_{m''}H_{2m''}-OOC-CHR_6CH_2-$$

in which
$R_6$ is hydrogen or methyl and
$m''$ is 2, 3 or 4; and
$Z_b$ is a group of the formula

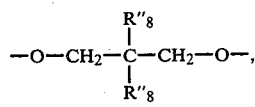

in which $R''_8$ is $C_{1-4}$alkyl, or a group of the formula

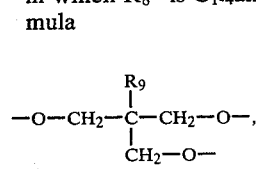

where $R_9$ is methyl or ethyl,
X is oxygen when Z is $Z_a'''$ and oxygen or sulphur when Z is $Z_b$, and
r is 2 when Z is $Z_a'''$ and 2 or 3 when Z is $Z_b$.

2. Flameproofed polyester according to claim 1 wherein, in the compound of formula I,
$R_1$ and $R_2$ are, independently, $C_{1-4}$alkyl or phenyl,
$R_3$ is hydrogen or $C_{1-3}$alkyl, and
$R_4$ and $R_5$ are hydrogen.

3. Flameproofed polyester according to claim 2 wherein, in the compound of formula I,
$R_1$ and $R_2$ are, independently, $C_{1-4}$alkyl, and
$R_3$ is hydrogen, n-propyl or isopropyl.

4. Flameproofed polyester according to claim 3 wherein, in the compound of formula I,
$R_1$ and $R_2$ are methyl, and
$R_3$ is hydrogen.

5. Flameproofed polyester according to claim 2, produced by polycondensing the polyester precursors in admixture with the compound of formula I.

6. Flameproofed polyester according to claim 2, produced by blending the compound of formula I with molten polyester.

7. Flameproofed polyester according to claim 2 in the form of powder, granules, pellets, fibers, film, foam, molded articles or woven or knitted textile fabric, which forms are free from cellulose and cellulose derivatives when Z in the compound of formula I is $Z_b$.

8. Flameproofed polyester, according to claim 1 containing, as a flameproofing agent, a flameproofing effective amount of at least one compound of formula I,

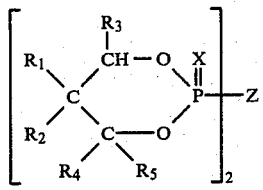

wherein
$R_1$ and $R_2$ are, independently, hydrogen; $C_{1-4}$alkyl; phenyl; or $R_1$ and $R_2$, together with the carbon atom to which they are attached, form a cyclohexylidene are cyclohexenylidene ring;
$R_3$ and $R_4$ are, independently, hydrogen or $C_{1-4}$alkyl;
$R_5$ is hydrogen or methyl, provided that when $R_1$ and $R_2$, together with the carbon atom to which they are attached, form a cyclohexylidene or cyclohexenylidene ring, each of $R_3$, $R_4$ and $R_5$ is hydrogen;
Z is a group $Z_a'''$ or $Z_b''$, where
  $Z_a'''$ is $C_{1-10}$-alkylene, $C_{6-8}$ cycloalkylene, 2-butenylene or a group of the formula $$-CH_2CHR_6-COO-C_{m''}H_{2m''}-OOC-CHR_6CH_2-$$

in which
$R_6$ is hydrogen or methyl and
$m''$ is 2, 3 or 4; and
$Z_b''$ is a group of the formula

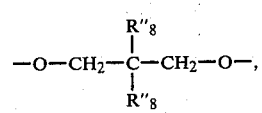

in which
$R''_8$ is $C_{1-4}$alkyl; and
X is oxygen when Z is $Z_a'''$ and oxygen or sulphur when Z is $Z_b''$.

9. Flameproofed polyester according to claim 8 wherein, in the compound of formula I,
$R_1$ and $R_2$ are, independently, $C_{1-4}$alkyl or phenyl,
$R_3$ is hydrogen or $C_{1-3}$alkyl, and
$R_4$ and $R_5$ are hydrogen.

10. Flameproofed polyester according to claim 9 wherein, in the compound of formula I,
$R_1$ and $R_2$ are, independently, $C_{1-4}$alkyl, and
$R_3$ is hydrogen, n-propyl or isopropyl.

11. Flameproofed polyester according to claim 10 wherein, in the compound of formula I,
$R_1$ and $R_2$ are methyl, and
$R_3$ is hydrogen.

12. Flameproofed polyester according to claim 8 wherein the compound of formula I is a compound of the formula

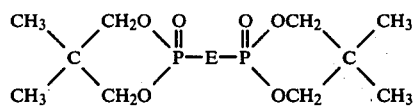

in which E is $C_{1-10}$alkylene.

13. Flameproofed polyester according to claim 8 wherein the compound of formula I is a compound of the formula

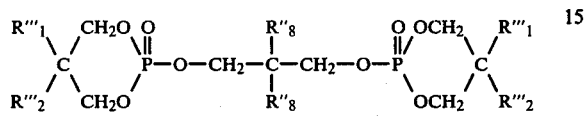

wherein $R_1'''$ and $R_2'''$ are, independently, $C_{1-3}$alkyl.

14. Flameproofed polyester according to claim 13 wherein $R_1'''$, $R_2'''$ and $R_8''$ are methyl.

15. Flameproofed polyester according to claim 8 wherein, in the compound of formula I, Z is $Z_a'''$.

16. Flameproofed polyester according to claim 1, 13, or 14 wherein the amount of flameproofing agent is from 1% to 5%, based on the weight of the polyester substrate.

17. A master batch composition comprising from 20% to 90% by weight of at least one compound of formula I, as defined in claim 8, and up to 80% by weight of polyester.

18. A method of producing flameproofed polyester comprising incorporating into the polyester before, during or after polymerization, a flameproofing effective amount of at least one compound of formula I,

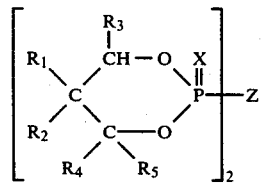

wherein
$R_1$ and $R_2$ are, independently, hydrogen; $C_{1-4}$alkyl; phenyl; or $R_1$ and $R_2$, together with the carbon atom to which they are attached, form a cyclohexylidene or cyclohexenylidene ring;
$R_3$ and $R_4$ are, independently, hydrogen or $C_{1-4}$alkyl;
$R_5$ is hydrogen or methyl, provided that when $R_1$ and $R_2$, together with the carbon atom to which they are attached, form a cyclohexylidene or cyclohexenylidene ring, each of $R_3$, $R_4$ and $R_5$ is hydrogen;
Z is a group $Z_a'''$ or $Z_b''$, where
$Z_a'''$ is $C_{1-10}$-alkylene, $C_{6-8}$cycloalkylene, 2-butenylene or a group of the formula

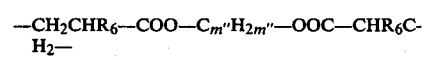

in which
$R_6$ is hydrogen or methyl and
$m''$ is 2, 3 or 4; and
$Z_b''$ is a group of the formula

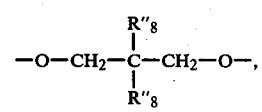

in which $R_8''$ is
$C_{1-4}$alkyl; and
X is oxygen when Z is $Z_a'''$ and oxygen or sulphur when Z is $Z_b''$.

19. A method according to claim 18 wherein the compound of formula I is incorporated into the polyester by polycondensing the polyester precursors in admixture with said compound.

20. A method according to claim 18 wherein the compound of formula I is incorporated in the polyester by blending it with molten polyester.

21. Flameproofed polyester according to claims 8, 1, 9, 11 or 13 produced by polycondensing the polyester precursors in admixture with the compound of formula I.

22. Flameproofed polyester according to claims 8, 1, 9, 11 or 13 produced by blending the compound of formula I with molten polyester.

23. Flameproofed polyester according to claims 8, 1, 9, 11 or 13 in the form of powder, granules, pellets, fibers, film, foam, molded articles or woven or knitted textile fabric, which forms are free from cellulose and cellulose derivatives when Z in the compound of formula I is $Z_b$.

* * * * *